United States Patent [19]
Gill

[11] Patent Number: 5,178,018
[45] Date of Patent: Jan. 12, 1993

[54] SYSTEM FOR MEASURING THE TIME FOR A SIGNAL TO PASS BETWEEN TWO SPACED POINTS IN A FLUID

[75] Inventor: Michael J. Gill, Hampshire, United Kingdom

[73] Assignee: British Gas plc, London, United Kingdom

[21] Appl. No.: 596,011

[22] Filed: Oct. 11, 1990

[30] Foreign Application Priority Data

Oct. 31, 1989 [GB] United Kingdom ............... 8924517

[51] Int. Cl.⁵ .................................................. G01F 1/66
[52] U.S. Cl. ................................... 73/861.28; 73/596
[58] Field of Search ............... 73/597, 861.27, 861.28, 73/861.29

[56] References Cited
U.S. PATENT DOCUMENTS 4,424,715 1/1984 Hansen ........................... 73/861.28
4,787,252 11/1988 Jacobson et al. ................ 73/861.28

Primary Examiner—Donald O. Woodiel
Attorney, Agent, or Firm—Oblon, Spivak, McClelland, Maier & Neustadt

[57] ABSTRACT

A measurement system for measuring the time for a signal to pass between two transducers TDR1,2 to allow fluid speed or flow to be determined in a gas meter for example. Each transducer can transmit or receive signals. The system is controlled by a microcontroller 31 and a signal with a phase change acts as a marker which is transmitted from transmitter 21 via matching stage 22,23 from one transducer and is received by the other. On receipt via the matching stage and amplifier 24 it is sampled by capacitor array 25 and detected in detector 29. Amplitude information from array 25 is made available to the microcontroller to compute time of signal travel and hence flow rates.

31 Claims, 9 Drawing Sheets

SYSTEM FOR MEASURING THE TIME FOR A SIGNAL TO PASS BETWEEN TWO SPACED POINTS IN A FLUID

The invention relates to a measurement system for measuring the speed and/or volume of fluid passing between two transducers.

In our copending UK patent application 8813640, a system and method is described for measuring fluid in a device suitable, inter alia, for gas metering. The arrangement determines the speed/volume of gas by detecting the time of flight of an ultrasonic signal in both directions between first and second transducers and uses this result to compute the gas speed and the volume of gas consumed. The present system is concerned with providing a modified system to that described in our copending application.

According to the invention there is provided a system for measuring the time for a signal to pass between two spaced points in a fluid comprising, transmitter means for generating a signal including a plurality of cycles or pulses with a phase change therein acting as a marker, first transducer means for transmitting the generated signals, second transducer means spaced from the first transducer means for receiving the transmitted signal, and means for sensing the received signal, said sensing means including means for detecting the phase change marker and means for retaining amplitude information on the received signal to assist in measuring the time period for the signal passage through the fluid.

Further according to the invention there is provided a method of measuring the time for a signal to pass between two spaced points in a fluid comprising, generating a signal including a plurality of cycles or pulses with a phase change therein acting as a marker, transmitting the generated signal through the fluid via a first transducer, receiving the transmitted signal from a second transducer after passage through the fluid, and sensing the received signal, said sensing step including detecting the phase change marker and retaining amplitude information on the received signal to assist in measuring the time period for the signal passage through the fluid.

Further according to the invention there is provided a fluid measurement device comprising, first and second spaced transducer means, transmitter and receiving means for transmitting and receiving signals in both directions between said transducer means, switching means for allowing each transducer means to be periodically used for either transmission or reception and matching means for transmission and reception to ensure that transducer characteristics are substantially constant for both transmitting and receiving modes of operation.

The invention will now be described by way of example with reference to the embodiments described in the accompanying drawings in which.

Figure 1:
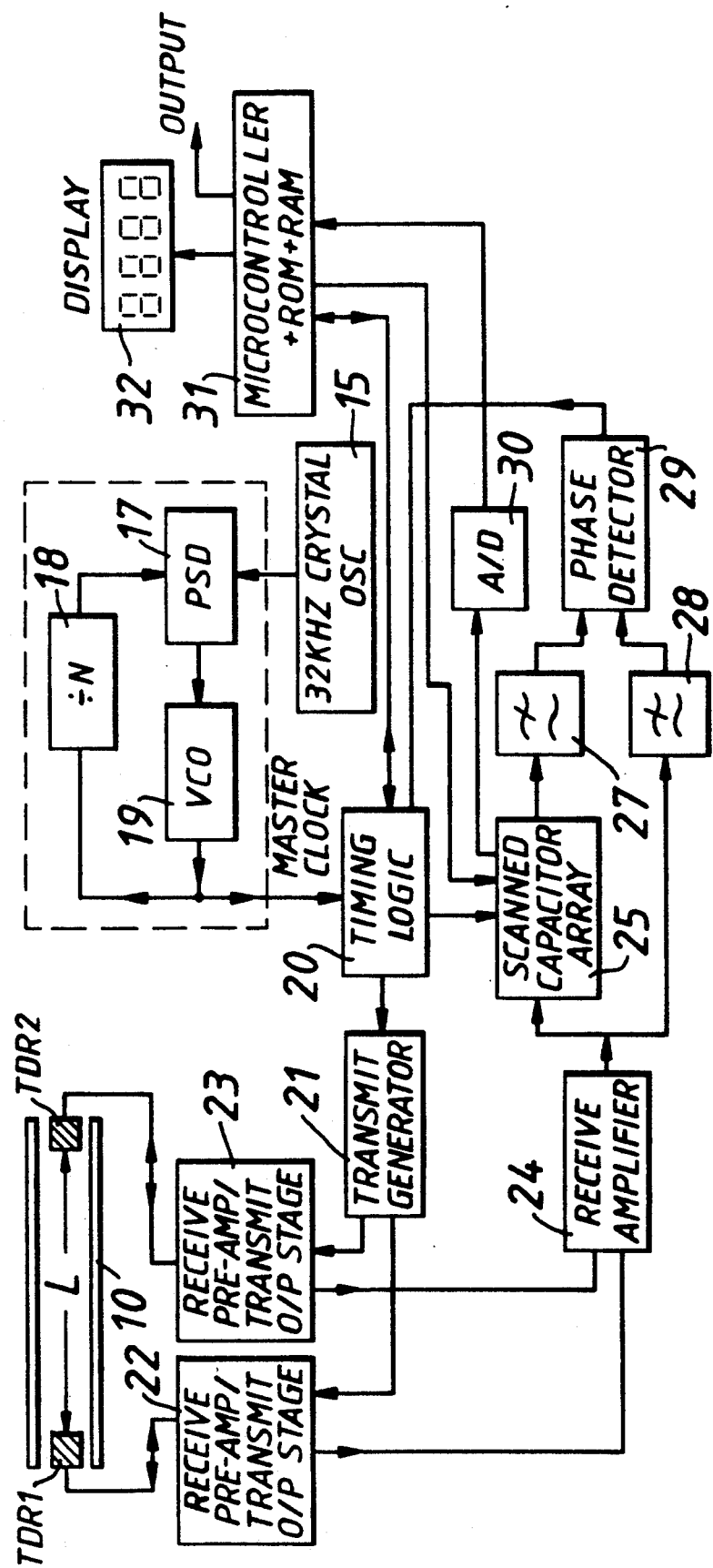
FIG. 1 shows a first configuration for measurement of fluid flow.

The configuration of FIG. 1 shows a fluid speed measurement arrangement employing two acoustic transducers TRD1,2 (e.g. piezo-electric devices) in a duct 10 spaced from each other by a distance L. These acoustic transducers are operable at ultrasonic frequencies.

The system includes a crystal oscillator 15 which provides a stable reference signal source (e.g. 32 kHz). This is provided for the phase locked loop (PLL) within the broken lines and comprising a phase sensitive detector 17, a divider 18 and a voltage controlled oscillator (VCO) 19.

The VCO 19 is configured to provide a fixed frequency output (e.g. 1.44 MHz) controlled by its input voltage. This frequency is fed back via divider 18 (e.g. divide by 44) to give a frequency corresponding to the accurate crystal oscillator reference frequency. These frequencies are compared in detector 17 and its voltage will be adjusted if any error is present to pull the VCO into line.

The output of VCO 19 provides the master clock frequency of the system. This master clock is made available to a timing logic block 20 which can pass this to other system blocks when required or provide control signals dependent on internal logic (or as instructed by a microprocessor/controller 31). As each transducer is used alternatively to transmit and receive a carrier wave or burst of signals, typically pulses, each transducer will have access to transmit and receive circuitry and the timing logic will determine, under microprocessor control, when these events will occur. A transmit generator 21 will receive master clocks from timing block as well as instructions to transmit and the transducer selected for transmission. The transmitter output will comprise a burst of pulses (e.g. at a frequency of 180 kHz) with the phase of the pulses being inverted partway through the transmission to act as a marker and this burst will pass to either interface block 22 or 23. Each of blocks 22 and 23 include a transmission stage for the associated transducer and a receiving preamplification stage for handling the received signal generated as a result of passage of the ultrasonic output through the duct 10.

The received signal is further amplified in common amplifier 24 and passed to a scanned capacitive array (SCA) 25 which, as described in more detail below, is provided with 'snapshots' of respective portions of cycles of the incoming waveforms. As this picture is built up over several cycles it give a filtering effect to the incoming information. The information built up and stored by the capacitors serves two purposes, firstly it acts as a phase memory for a reference via a filter 27 and a phase detector 29 for determining a phase change and secondly it acts as an information memory source after phase change detection for use by the microprocessor 31 via an analogue to digital (AD) converter 30. The microprocessor 31 uses the held information to derive additional timing information to ensure greater accuracy of time of flight to be determined, as described below.

The phase detector 29 also receives the output of a low-pass filter 28 at its other input and the two inputs allow the detector to determine when a change of phase has occurred (indicative of the returning marker). The signal from the capacitor array 25 is delayed with respect to the signal at the other input to the detector 29 which aids the detection of the phase change of the undelayed signal.

On detection of the phase change, the detector output causes the logic block 20 to send an inhibit or freeze signal to array 25 to prevent further signal samples being stored therebye and allows the stored values to be retained and available to the microprocessor 31. The microprocessor will make use of information on the number of master clock pulses that have occurred during the flight time together with additional information derived from the stored voltages on the capacitor array 25 to determine transit time. This combined information provides increased resolution in flight time computation and the results in terms of speed or fluid flow rate, for example, can be made available to a display 32. The output from microcontroller 31 may also be made available for remote access, for example. Various aspects of the system operation and construction will now be considered in more detail.

Figure 2:
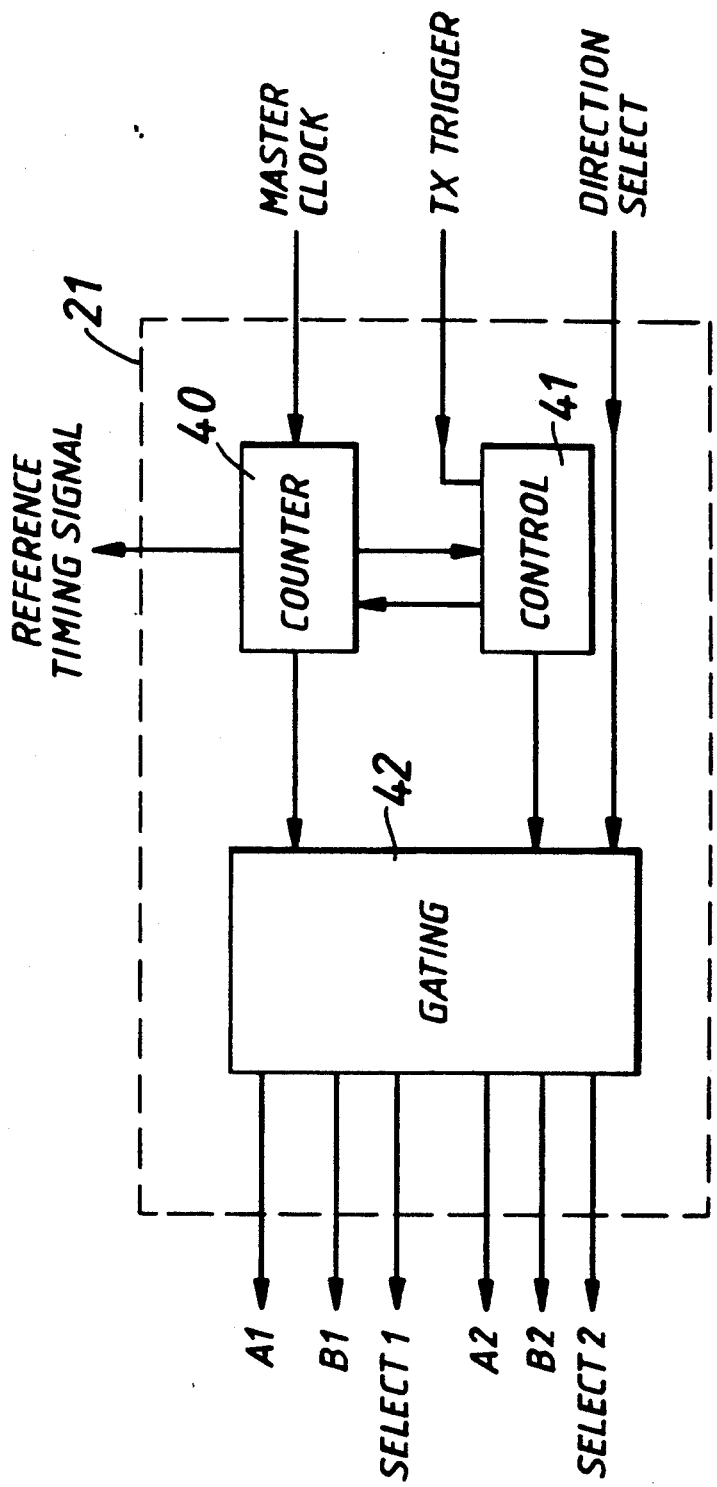
FIG. 2 shows the transmit generator of FIG. 1 in more detail.

As already described, the transmit generator 21 will be required to transmit a burst of information to alternate transducers and a suitable configuration for the generator 21 is shown in FIG. 2. This comprises a counter 40, a control block 41 and a gating block 42. The timing logic block 20 of FIG. 1 provides three inputs to the generator block 21. These are the master clock pulses, a transmit trigger and a direction select signal. The counter 40 receives and counts the master clock pulses (see FIG. 3a) following the transmit trigger (see FIG. 3b) and provides a series of pulses (see FIGS. 3c and 3d) for transmission via gating block 42.

Figure 3:
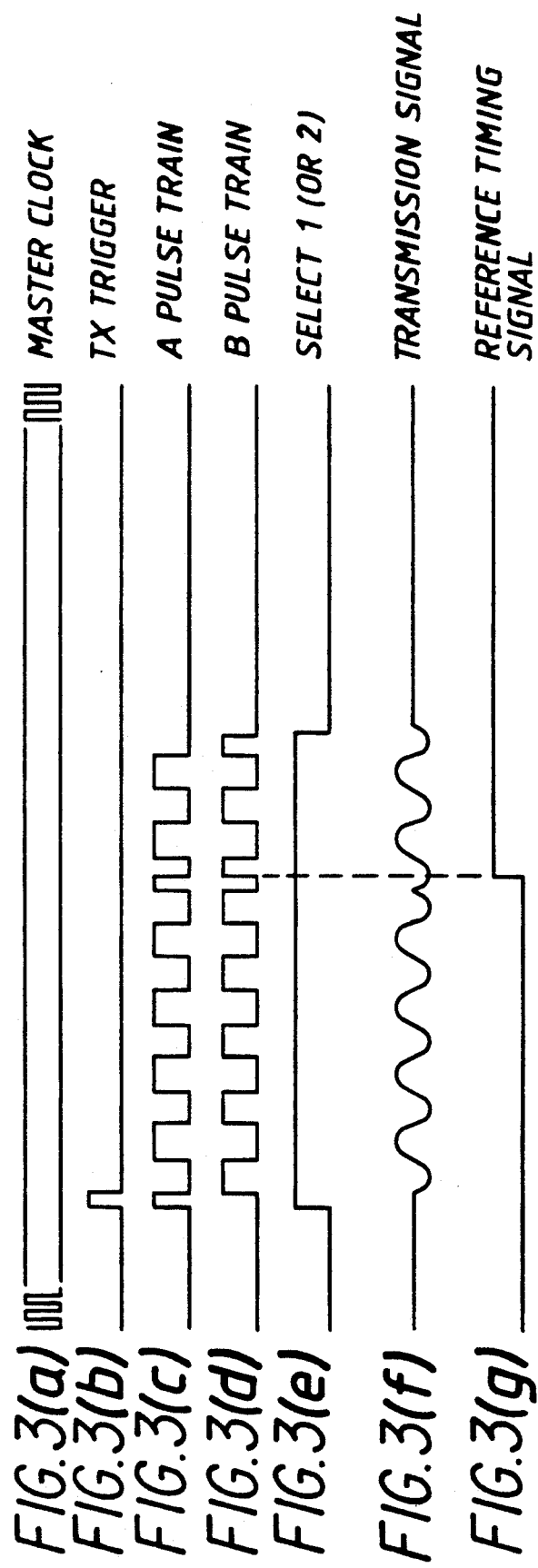
FIGS. 3a–3g show waveforms associated with transmission.

The counter 40 will provide the timing reference signal (see FIG. 3g) which will be the start point from which the time of flight is calculated. The master clock pulses of FIG. 3a are continually generated to act as a system reference source. The antiphase pulse trains A and B of FIGS. 3c and 3d are used in the drive circuitry within blocks 22 or 23 of FIG. 1 as described below. A select signal (see FIG. 3e) is also provided to select which transducer (TDR1 or TDR2) is used on this particular occasion for transmission (the other transducer being available for reception). The waveform for transmission (after passing through matching components within blocks 22 or 23 of FIG. 1) will be as represented by FIG. 3f.

Figure 4:
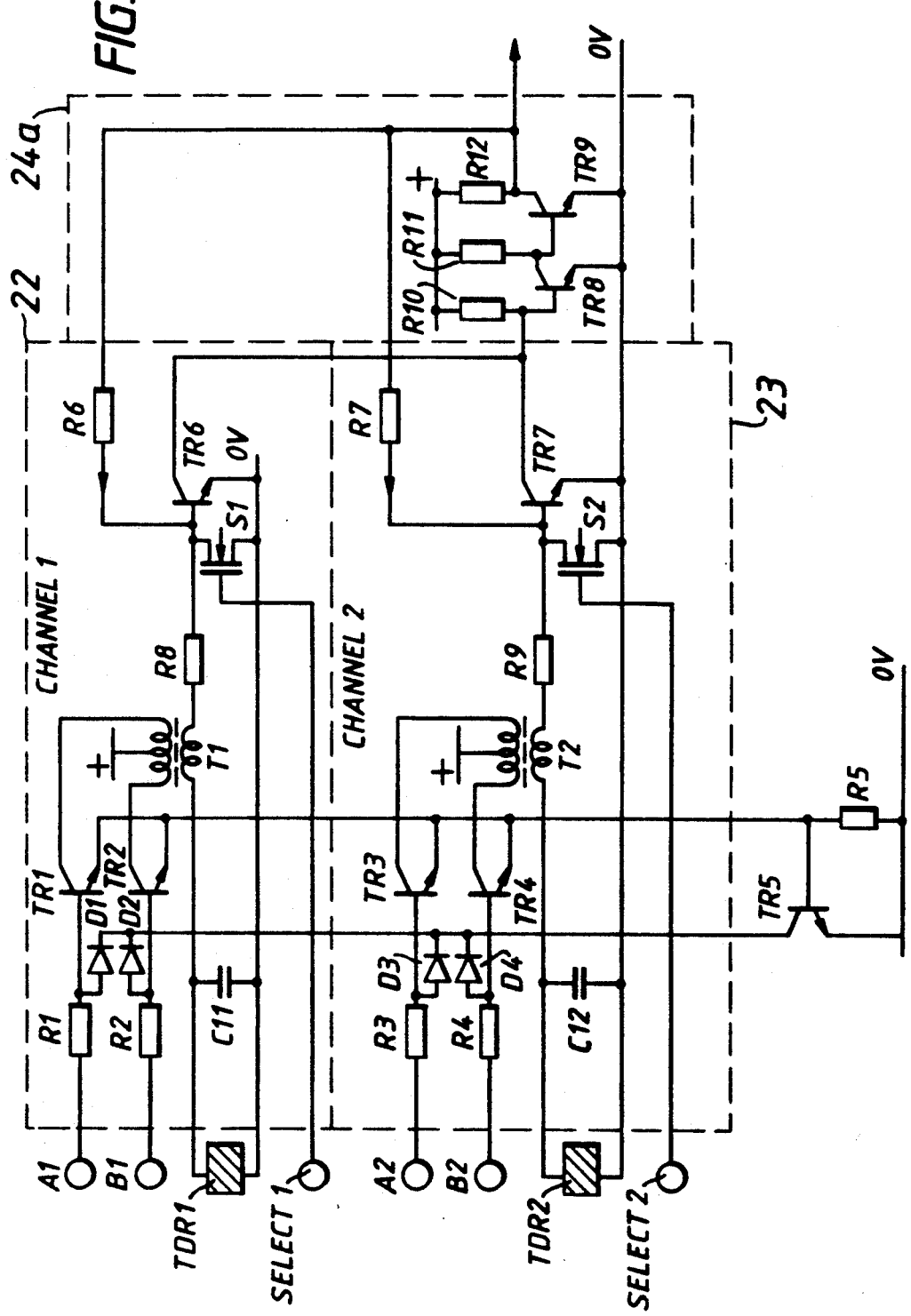
FIG. 4 shows the transmission/reception stages of FIG. 1 associated with the transducers, in more detail.

Thus it can be seen that the pulse trains and the transmission signal derived therefrom each comprise a number of cycles followed by an inverted signal, this followed by further cycles. In the example of FIGS. 3c and 3d there are four pulse cycles before the inversion and then two more pulse cycles thereafter. In a preferred arrangement, the system would provide an initial 16 cycles before inversion and eight cycles thereafter as determined by control 41. The counter 40 receives the master clocks at 1.44 MHz and it counts each 8 clock pulses and provides an output thereafter to provide a divide by eight function. The pulse trains of FIGS. 3c and 3d are produced at a rate of 180 kHz, suitable for use by the ultrasonic transducers TDR1 and TDR2 after suitable matching in blocks 22 or 23. A configuration for these blocks is shown in FIG. 4, somewhat simplified for the sake of clarity.

Each transmit output stage/receive pre-amp block 22 and 23 has identical components. Block 22 receives signals A1, B1 and Select 1. A1 and B1 are connected via resistors R1 and R2 to transistors TR1 and TR2 which have outputs to transformer T1. The other winding of T1 is connected to transducer TDR1. Capacitor C11 is connected across TDR1. Resistor R8 is connected to field effect transistor (FET) S1 which operates as a switch in dependence on the Select 1 input. T1, C11 and R8 act as matching network components for transmission and reception to ensure optimum operating characteristics. Transistors TR1 and TR2 together with diodes D1 and D2 are connected to a constant current regulator comprising transistor TR5 and resistor R5.

Transistor TR6 provides a first amplification stage during reception of signals from TRD1 and this transistor output is connected to preamplifier stage 24a of amplifier 24. The preamp comprises transistors TR8 and TR9 with associated resistors R10–R12. Feedback is provided via resistor R6.

Block 23 is identical to block 22 and comprises resistors R3,R4,R7,R9, transistors TR3,4,7, transformer T2, capacitor C12, FET S2 and diodes D3,4. This block also has access to the constant current regulator TR5/R5 and the amplifier block 24. Resistor R9, transformer T2 and capacitor C12 provide the matching network.

For transmission in channel 1, TR1 and TR2 are alternately activated by signals A1 and B1 through R1 and R2. Emitter current is monitored by R5 and TR5 (common to both channels). When current reaches the conduction threshold of TR5 (which it does within a few nSec of each positive edge of the incoming signal), TR5 conducts to reduce the base drive and form a current regulation loop. Power is coupled to the transducer via the centre tapped primary winding of T1, which forms part of the matching network associated with TDR1. The constant current nature of the excitation prevents any modification of the impedance characteristics of the matching network. During transmission, S1 is turned on by the Select 1 signal to provide a low impedance path for currents circulating in the matching network. S1 remains on during the reception period of the transmitted signal by the receiving transducer TDR2. The waveform for transmission is shown in FIG. 3f.

For reception of the transmitted signal (on channel 2), signals A2 and B2 are inactive and TR3 and TR4 are disabled. S2 is turned off, enabling the first amplifier transistor TR7. TR7,8 and 9 thus act as a high gain amplifier with negative feedback via R7. The heavy negative feedback ensures a very low input impedance to the matching network, comparable with that provided by S2 during transmission. The matching network is maintained substantially invarient for both transmission and reception in this way. Typically phase coherance of less than 0.1 degree can be maintained with normal component tolerances.

The channels 1 and 2 will reverse operation during the next transmission burst, with channel 2 transmitting and channel 1 receiving the ultrasonic signals under selection control.

By operating the transducers at a tightly controlled impedance on both transmit and receive with T1 and T2 secondaries assisting in impedance matching and by sharing circuits where possible and with transducer Transmit-Receive reciprocity, timing offsets as a source of error are virtually eliminated. By using the master clocks as the source of transmit signals phase errors therebetween are eliminated.

Figure 5:
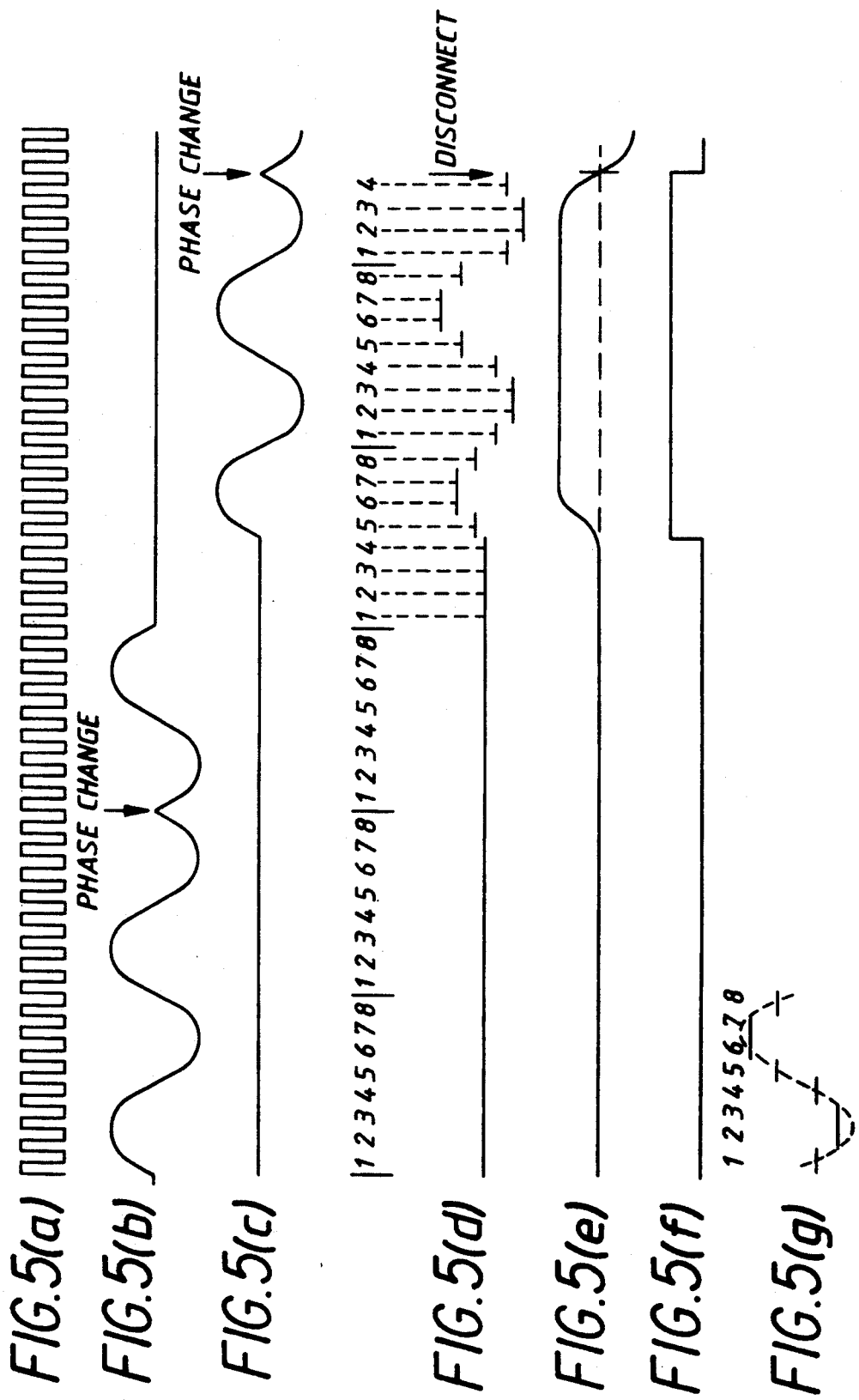
FIGS. 5a–5g shows waveforms associated with reception and detection following transmission.

As already explained above with regard to FIG. 1, the system is required to determine the period between transmission and reception of the transducer signal having travelled through the duct 10 (i.e. transit time). This time period can be represented by comparison of FIGS. 5b and 5c waveforms. The number of cycles on either side of the phase change has been reduced to enable a more detailed examination of the area of the waveform adjacent the phase change to be effected. The waveform of FIG. 5a is the master clock train (e.g. at 1.44 MHz). FIG. 5b represents the transmitted signal and 5c represents the returning signal delayed by the period taken to travel through the duct between the transducers.

Figure 6:
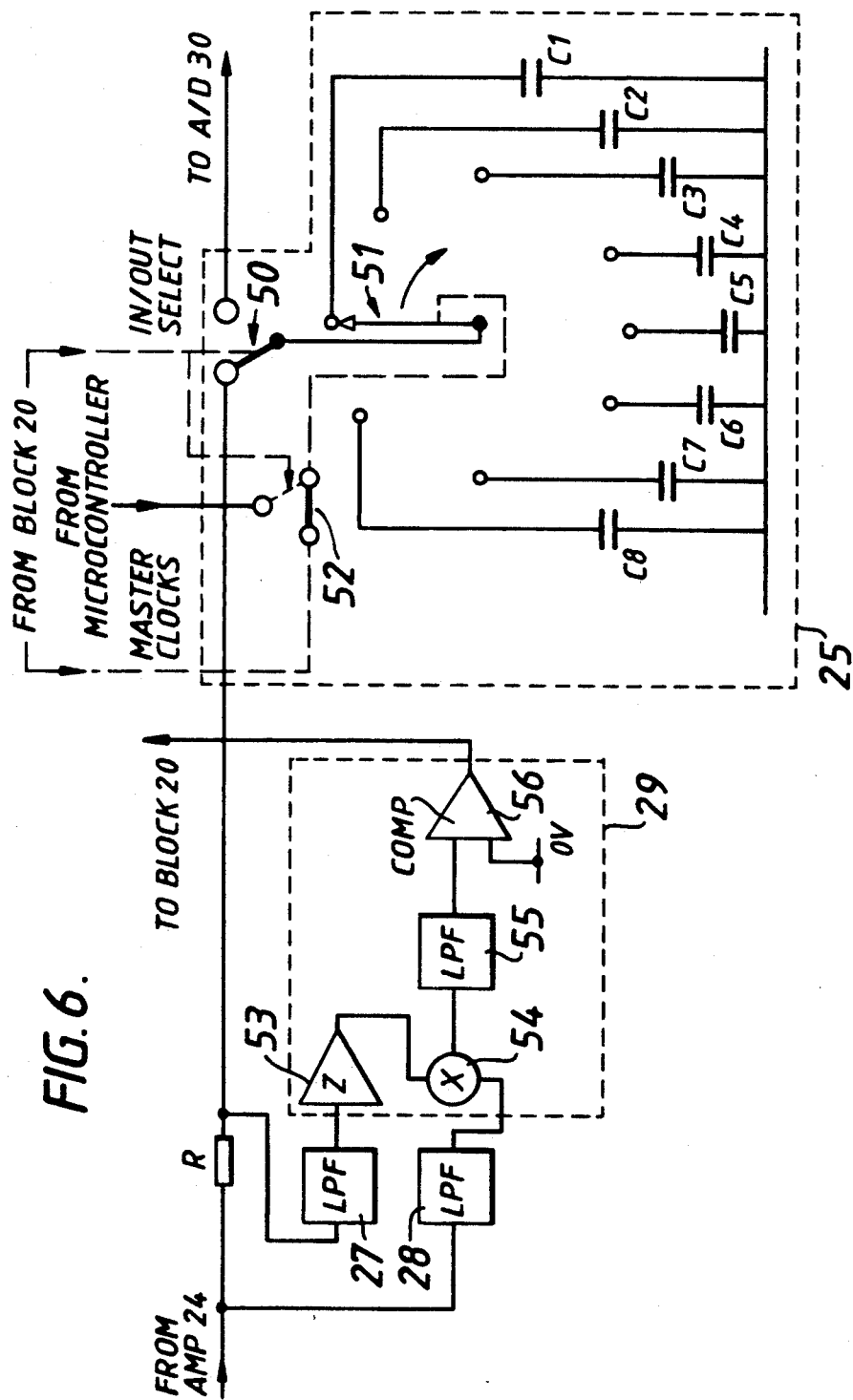
FIG. 6 shows the scanned capacitor array and detection aspects of FIG. 1 in more detail.

Array 25 of FIG. 1 is shown in detail in FIG. 6 and comprises eight capacitors 1-8 which are sequentially scanned, each capacitor storing a voltage which represents a snapshot of the instantaneous voltage applied to it as the incoming received voltage waveform of FIG. 5c progresses. In practice each capacitor is connected via a common resistor R so that these form a simple RC integrating network that enables averaging of each capacitor sample voltage from one wave to the next. This averaging over a number of waves gives a filtering effect to the stored voltage. This effect can be seen from the voltage on the capacitors over several cycles. Thus the first three sequencing cycles of FIG. 5d show no voltage present on the capacitors 1-8, but as the returning ultrasonic signal occurs the capacitors 5-8 in the fourth cycle begin to hold a sampled voltage.

Capacitors 1-4 do not receive a change in voltage till the fifth cycle. It can be seen that capacitors 5-8 in the fifth cycle have accrued a higher (positive) voltage and capacitors 1-4 accrue a negative voltage which will continue in subsequent cycles. Only two waves are shown prior to the phase change in this simplified waveform, but in practice there would typically be 16 wave cycles before the phase change so the averaging period would be substantially longer than shown. This gives good noise rejection with narrow receiver bandwidth (approx 4 kHz).

On detection of a phase change by the phase detector 29 of FIG. 1, no further samples are applied to the capacitors due to disconnection of the input (see FIG. 5d) and the voltages thereon are held to be used to assist in calculating the transit time.

A configuration for the capacitor array and detection mechanisms is shown in FIG. 6.

As shown, the input from amplifier 24 is passed via the common resistor R to the capacitors C1-C8 via switches 50 and 51. Switch 51 receives master clock pulses from timing block 20 of FIG. 1 and switch 50 is also controlled by this block 20. Switch 52 is also controlled by block 20 to allow the microcontroller 31 to be able to actuate switch 51 when the receiving sequence is completed. The switch 51 will normally step at the master clock rate (e.g. 1.44 MHz) so that, as shown in FIG. 5d, each capacitor will be connected for ⅛th of the cycle period of a received waveform. The switch 51 will continue to rotate until inhibited by block 20 (as a result of a detected phase change). The phase inversion will be detected by detector 29 which comprises a limiting amplifier 53, a synchronous detector 54, a low pass filter 55 and a comparator 56. The synchronous detector 54 receives inputs from the low pass filters 27 and 28.

Although filter 28 receives its input directly from amplifier 24, filter 27 receives its input from the RC network. The dynamic characteristic of the sequencing capacitors' is equivalent to that of a resonant LC circuit and acts as a phase memory to operate as a reference input to the phase detector 29. The synchronous detector 54 output passes through filter 55 (see waveform of FIG. 5e) and is detected by comparator 56 (see FIG. 5f) to provide the detection signal for the timing block 20 of FIG. 1. Block 20 then disconnects switch 50 from the incoming signal from amplifier 24 and connects switch 52 to the microcontroller 31 so the stored capacitor voltages can thereafter be connected in turn (using switch 51) to analogue to digital converter 30 of FIG. 1, via switch 50, to allow measurement of each of these voltages. The microprocessor 31 of FIG. 1 will have knowledge from block 20 of how many master clock pulses have occurred during the period between transmission and detection of the returning phase inversion marker and this gives a timing period accurate to within 1 clock period of the master clock, which is ⅛th of the ultrasonic signal frequency. Thus with a 1.44 MHz clock, the time of flight accuracy would be expected to be within a usec (i.e. a millionth of a second). In practice due to slight waveform drift for example, this is more likely to be accurate to two or three clock pulses (e.g. 5 millionths of a second).

Whilst this is accurate enough for some applications, when dealing with gas metering for example, even greater accuracy can be required and this can be achieved by investigating the voltages held on the capacitor array as passed to the microprocessor 31 when switch 50 is in the opposite position to that shown in FIG. 6 and switch 51 is then stepped by the microprocessor 31 via switch 52. Their digital value can be used to determine the phase shift of the wave during transit and this is used to give fine adjustment to the time of flight values as now explained.

As the master clock is divided by 8 to generate the transmit signal this ensures it is in phase with the master clock. The master clock is also used to step switch 51 so that the first switch cycle starts at the beginning of the transmit waveform (see FIGS. 5b and 5d) and continues till a detected phase reversal. The voltages stored on each capacitor averaged over several cycles mimic the phase of the received waveform. Thus the values on the capacitor array at disconnection in the sequence 1-8 will be as shown in FIG. 5g.

The broken line represents a reconstructed waveform using these voltages. Comparing the waveforms of FIG. 5g with 5b will show that in this example this is 180 degrees out of phase with the transmitted waveform and this is used to adjust the value of the computed transit period. Thus if 701 master clock pulses had been counted between the transmitted and received phase inversion, then this would be a transit time of 701/8 = 87.6 utrasonic wave periods.

However from FIG. 5g it is seen that a 180 degree phase shift has occurred which is 0.5 of a full wave of 360 degrees. Thus 0.5 is the more accurate result for the part cycle and so the resolution of the result has been improved to give a true result of 87.500 rather than 87.6 cycles. Thus the phase measurement which has been averaged over several cycles (in the preferred arrangement over 16 cycles) will override the coarse value provided by the master clock alone and takes into account any drift between cycles.

The voltages on the capacitors are each converted into an 8 bit value in the A/D converter 30 of FIG. 1. The phase angle of the stored waveform is computed using a single point Fourier transform, for example, on the digital voltage values and the resultant resolution is approximately 5 nS, an improvement of 1000 times over that achieved using the clocks alone.

Where the number of clock pulses is being computed from the transmit trigger pulse (FIG. 3b) and where 16 cycles are being produced before the transmitted phase inversion marker, there will be a need to subtract 16 cycles, which corresponds to 16×8 master clock pulses which is 128 pulses. Thus in the above example, the number of pulses counted would have been 701+128=829 from the transmit trigger. At a clock rate of 1.44 MHz this 128 count will require a 88.88 uS period and the 701 pulse count will require a 486.8 uS period.

Sine and Cosine coefficients of the reconstructed sine wave are calculated using the following equation (where v0 to v7 are the digital values of the capacitor array in the range 0 to 255.

Sine Coeff=(v2−v6)+0.707(v1+v3−v5−v7)

Cosine Coeff=(v0−v4)+0.707(v1+v7−v3−v5)

To determine the phase angle of the cycle derived from the capacitors, the magnitudes and signs of the sine and cosine coefficients are determined and used to calculate which octant the cycle is in.

| Octant | 0 | 1/8 | 2/8 | 3/8 | 4/8 | 5/8 | 6/8 | 7/8 |
|---|---|---|---|---|---|---|---|---|
| Sine | | + | | + | | − | | − |
| Cosine | | + | | − | | − | | + |
| S > C | no | yes | yes | no | no | yes | yes | no |

1. If C>S and Cosine coeff and Sine coeff are both positive then fine count=arctan(sine/cos).
2. If C>S and Cosine coeff is positive but Sine coeff is negative then fine count=360 deg−arctan(sine/cos).
3. If C>S and Cosine coeff and Sine coeff are both negative then fine count=180 deg+arctan(sine/cos).
4. If C>S and Cosine coeff is negative but Sine coeff is positive then fine count=180 deg−arctan(sine/cos).
5. If S>C and Cosine coeff and Sine coeff are both positive then fine count=90 deg−arctan(cos/sine).
6. If S>C and Cosine coeff is positive but Sine coeff is negative then fine count=270 deg+arctan(cos/sine).
7. If S>C and Cosine coeff and Sine coeff are both negative then fine count=270 deg−arctan(cos/sin).
8. If S>C and Cosine coeff is negative but Sine coeff is positive then fine count=90 deg+arctan(cos/sin).

The coarse count derived from the master clocks and the fine count from the above are combined in binary form. To effect this, the coarse count is decremented until its 3 least significant bits (LSBs) match the 3 most significant bits (MSBs) of the fine count. The bottom 3 bits of the coarse count are then discarded and the coarse count shifted 7 times. Finally the fine count is added to the coarse count all under microprocessor control.

The combined count is now in terms of the 1.44 MHz master clock×128 giving a 184.3 MHz timing resolution. This can be improved with more A/D resolution. Thus 8 bit digitisation gives a resolution equivalent to approximately 1/1000th of a cycle. 10 bit conversion gives a resolution approximately 1/4000th of a cycle or about 1.3 nS at a 180 kHz frequency.

For computing the fluid speed from this transit time calculated in each direction the microprocessor employs the equation $$V=(L/2t1-L/2t2)$$

where t1 and t2 are transit times in each direction, V is velocity and L is the length between the transducers.

This formula can be modified where transducer delay or effective length reduction is significant.

Volume of gas can be determined from the speed results over a given time for a given duct bore size.

The speed of operation governed by the master clocks is sufficiently low to provide savings in cost and power consumption whilst giving equivalent resolution of 100 MHz or more.

To effect greater power savings, the system can be modified to allow the transducers to operate for short periods with relatively long rest periods, which is particularily useful where battery power is required to drive the system (e.g. in isolated locations).

Figure 7:
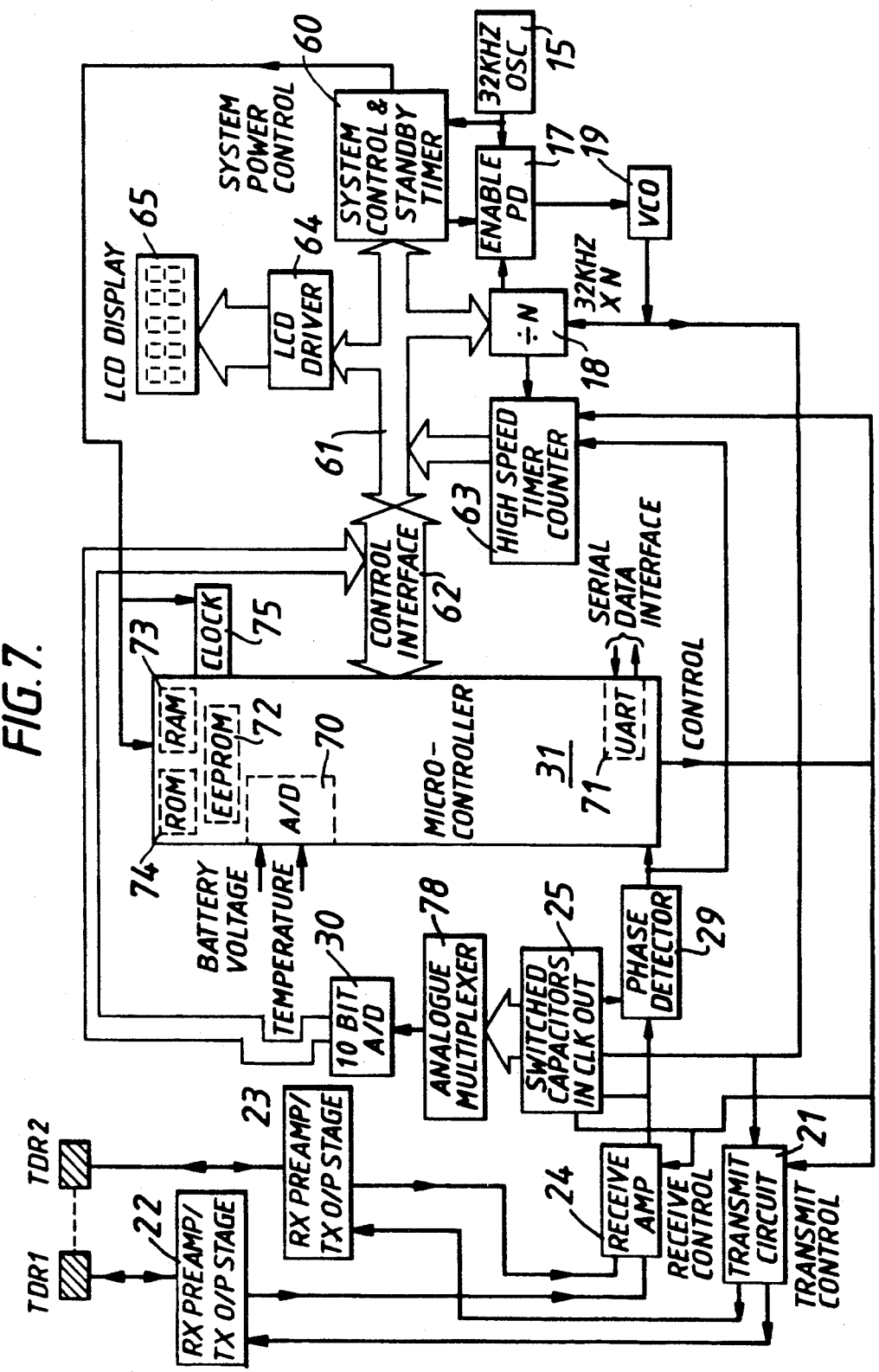
FIG. 7 shows an alternative embodiment to FIG. 1.

A further embodiment with low power requirements is shown in FIG. 7.

In this arrangement, the transducers TDR1,2 are connected to blocks 22, 23 and common receive amp 24 and transmit generator 21 as before. The phase detector 29 (with input filters, not shown) is connected to a counter 63. The microcontroller 31 (e.g. Hitachi type 68HC05) is selected for low voltage operation, so that the system can be powered by a single lithium cell, for example.

The counter is used to determine the number of master clocks during the period between transmission and detection of the phase inversion marker. The output of counter 63 is available for bus 61 which is connected to the microcontroller 31 via control interface 62.

A clock block 75 (e.g. 2 Mhz) is associated with the microcontroller and both receive inputs from timer 60. System control and standby timer 60 is provided to periodically enable the microcontroller and other components and at other times to put the system on standby and to provide an absolute time clock for the system.

The clock 75 is turned on shortly before the microcontroller 31 is enabled to ensure this has stabilised before microcontroller operation commences. The microcontroller 31, when enabled by timer 60 is then available to carry out the system sequence of transmission, reception, conversion, calculation and display. Once the sequence is completed the clock is switched off to save power.

The switched capacitor array 25 can have each voltage multiplexed via analogue multiplexer 78 to the A/D converter 30 which is preferably a 10 bit A/D to improve timing resolution. The converter output is available to the microcontroller via the control interface 62. A further A/D converter 70 may also receive inputs concerning battery voltage and temperature for monitoring or adjustment purposes. This is integral with controller 31 as is ROM 74, RAM 73 and electrically erasable programmable read only memory (EEPROM) 72.

A universal asynchronous receiver transmitter (UART) 71 is provided as a serial data interface.

A liquid crystal display (LCD) 65 is provided via driver 64. The driver has its own internal clock source.

The oscillator 15, phase detector 17, divider 18 and VCO 19 are provided as before. However, the divider ratio can be set via bus 61 and the phase locked loop comprising these blocks can be enabled when required by timer 60.

Figure 9:
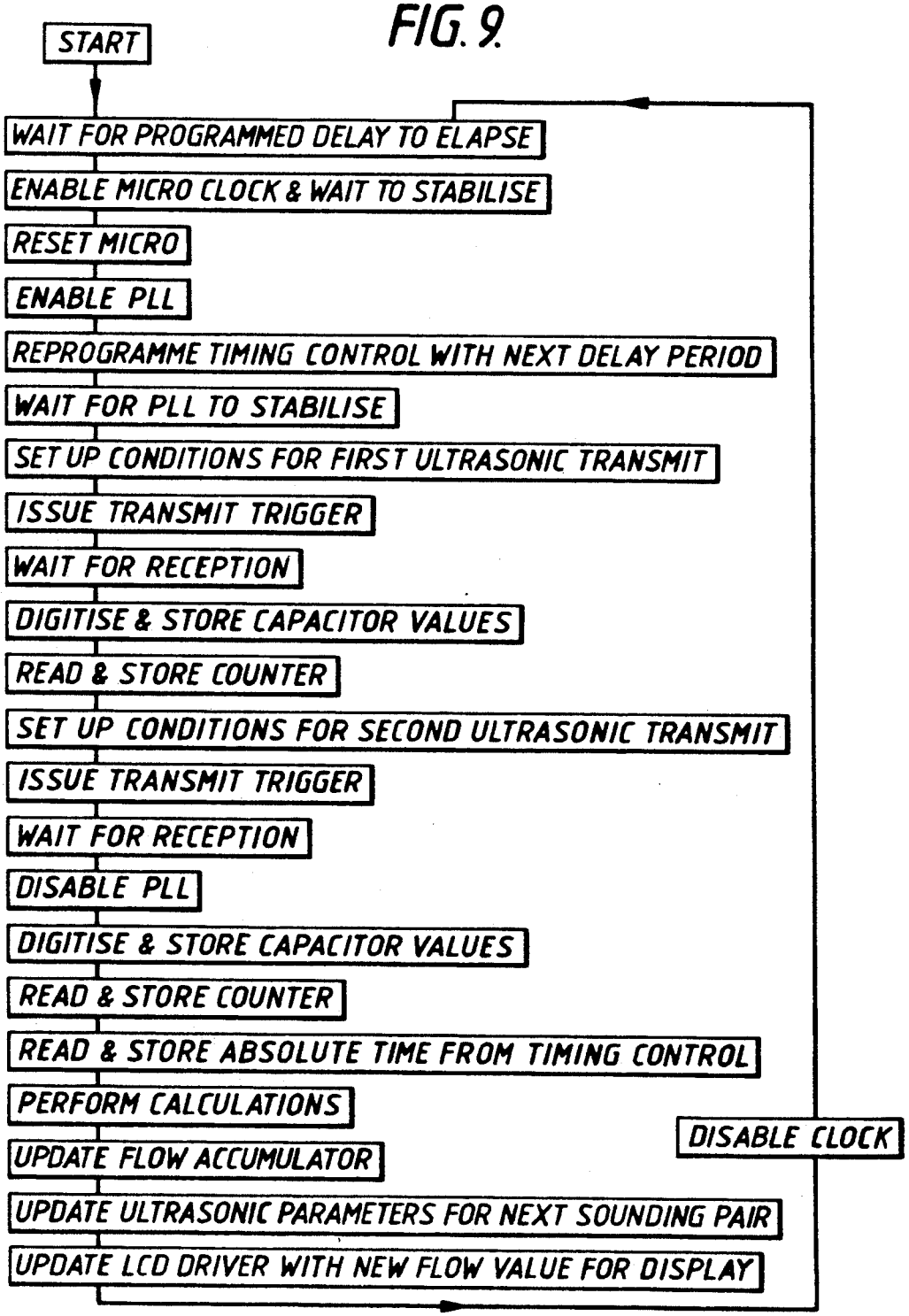
FIG. 9 shows a flowchart associated with FIG. 7.

Sequencing of the system is shown in the operational logic flowchart of FIG. 9.

The periodic use of the PLL and other components reduces power requirements and the only system blocks requiring continuous power are the LCD 65, the oscillator 15 and timer block 60. The microcontroller is continuously powered although its associated clock 75 will not be powered during standby to reduce power drain.

Figure 8:
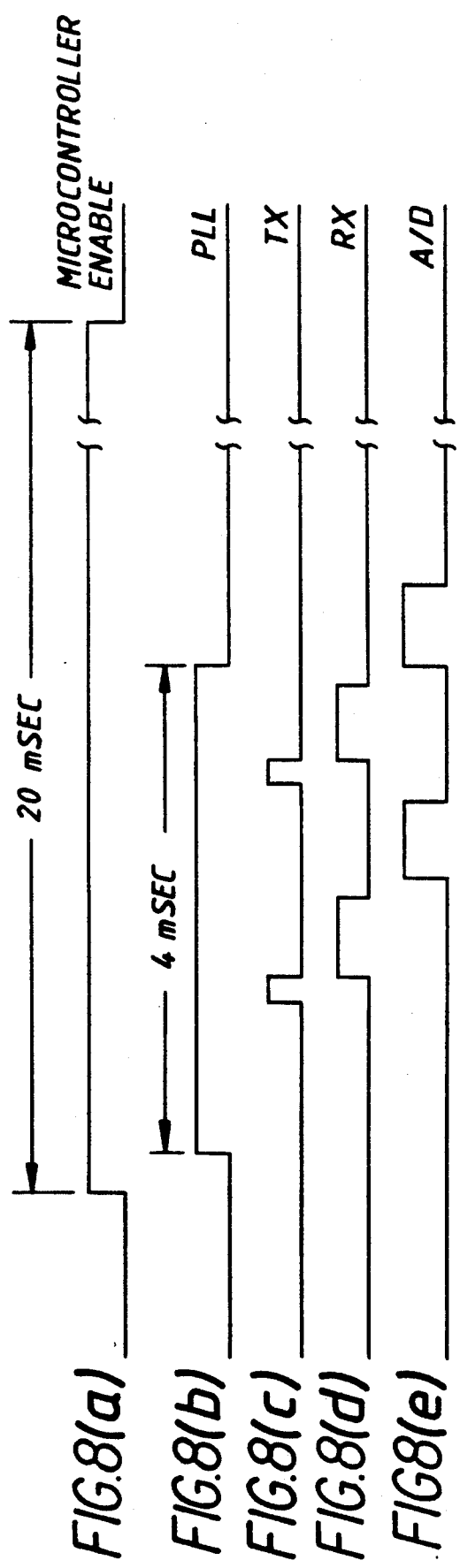
FIGS. 8a–8e show timing and other waveforms generated by the FIG. 7 configuration.

With such an arrangement the continuous current drain on standby is less than 50 uA. The system in practice is only active for less than 1/50th of the time, so minimising power requirements to allow a battery life of several years to be possible. The active periods can be seen from FIG. 8.

As already explained, during standby the timer 60 is active as is oscillator 15 which is needed as the clock input for the timer. Where a continuous display is required, LCD 65 will also be powered.

After a standby period determined by timer 60, the microcontroller 31 is enabled (see FIG. 8a) for a period of 20 mSec which is a sufficient to carry out transmission and detection of the ultrasonic pulses in both directions and to compute results therefrom.

Thus after turning on clock block 75 and enabling micro 31, the VCO is powered and the detector 17 enabled to pull the VCO 19 into line with the reference oscillator 15 (see FIG. 8b). After a few mSec (to enable the master clocks to settle) a transmit enable pulse is generated by control/timer 60 and this causes transmission during which the transducers are active. In practice a transmission will take place in either direction in this period (see FIG. 8c), so two active periods are shown.

Receiving circuitry will be active immediately after the transmission in each direction (see FIG. 8d).

The voltages on the 8 capacitors in the array will be converted into digital values after reception has ceased. Two such operations will occur, one for each direction of reception (see FIG. 8e).

After the 20 mSec period when the calculations have been completed and the results stored and displayed, the system goes back to standby for the next second, when the operations are repeated.

The PLL is active for about 4 mSec with the transducers being operative at various times in this period.

Transmission typically requires about 50 mA current but because of the brief period of activity, this averages over any given second to a mere 13 uA. Other periods are similarily brief, so that instead of having to cope with average power consumption of say 5 mA if the system was continuously active, this has been reduced to a very much lower value, typically 100 uA.

The use of the capacitor configuration to increase resolution also reduces power requirements because higher rate clocking would increase power consumption considerable in order to seek the resolution achieved by the present configuration.

I claim:

1. A system for measuring the time for a signal to pass between two spaced points in a fluid comprising:
    transmitter means for generating a signal including a plurality of cycles or pulses with a phase change provided therein acting as a marker;
    first transducer means for transmitting the generated signal with the marker therein;
    second transducer means spaced from the first transducer means for receiving the transmitted signal; and
    means for sensing the received signal, said sensing means including means for detecting the phase change marker and means for retaining amplitude information on the received signal to assist in measuring the time period for the signal passage through the fluid.

2. A system as claimed in claim 1, wherein the amplitude retaining means is arranged to sample amplitude information derived from a plurality of cycles.

3. A system as claimed in claim 1, wherein the retaining means includes a plurality of capacitors and selector means are provided to allow each capacitor to receive amplitude information at substantially the same relative cycle position during any given cycle, so as to average the amplitude information over a number of cycles.

4. A system as claimed in claim 3, wherein master clock generator means are provided to allow the transmitter means to generate a signal in synchronism therewith but at a lower frequency and to allow the selector means to select each capacitor in synchronism therewith to ensure correct cyclic positioning.

5. A system as claimed in claim 4, wherein the master clock generator means includes a phase locked loop arrangement linked to a lower frequency reference oscillator.

6. A system as claimed in any preceding claim, wherein timer means are provided to generate periodical standby and operational conditions, the standby condition being long relative to the operational condition to reduce power requirements.

7. A system as claimed in any one of claims 1 to 5, wherein inhibit means are provided to prevent the amplitude retaining means receiving further information following detection of the phase change to allow earlier amplitude information to be retained.

8. A system as claimed in any one of claims 1 to 5, wherein analogue to digital conversion means are provided to convert analogue amplitude information from the retaining means and computation means are provided for determining the relative signal phase derived from the amplitude information to provide accurate timing information.

9. A system as claimed 8, wherein the computation means includes timer means for initially determining the elapsed time between transmission and reception of the marker to allow this information to be used in combination with the phase information to more accurately determine this elapsed period.

10. A system as claimed in claim 8, wherein switching means are provided to allow the first and second transducer means to be used for both transmission and reception and said computation means being configured to use timing information from both signal travel directions to determine the speed or flow rate of the fluid.

11. A system as claimed in claim 10, wherein matching means are provided shared for both transmission and reception for each of the transducer means to ensure the transducer characteristics are substantially constant for both modes of operation.

12. A method of measuring the time for a signal to pass between two spaced points in a fluid comprising:
    generating a signal including a plurality of cycles or pulses with a phase change provided therein acting as a marker; transmitting the generated signal with the marker wherein through the fluid via a first transducer;

receiving the transmitted signal from a second transducer after passage through the fluid; and sensing the received signal, said sensing step including detecting the phase change marker and retaining amplitude information on the received signal to assist in measuring the time period for the signal passage through the fluid.

13. A method as claimed in claim 12, wherein the amplitude retaining step is arranged to sample amplitude information derived from a plurality of cycles.

14. A method as claimed in claim 12, wherein the retaining step includes allowing each of a plurality of capacitors to receive amplitude information at the same relative cycle position during any given cycle, so as to average the amplitude information over a number of cycles.

15. A method as claimed in claim 14, including generating a master clock to allow the signal for transmission to be generated in synchronism therewith but at a lower frequency and to allow selection of each capacitor in synchronism therewith to ensure correct cyclic positioning.

16. A method as claimed in claim 15, wherein the master clock generated is linked to a lower frequency reference source.

17. A method as claimed in any one of claims 12 to 16, including generating periodical standby and operational conditions, the standby condition being long relative to the operational condition to reduce power requirements.

18. A method as claimed in any one of claims 12 to 16, including an inhibit step to prevent further amplitude retention following detection of the phase change to allow earlier amplitude information to be retained.

19. A method as claimed in any one of claims 12 to 16, wherein analogue to digital conversion is provided to convert retained analogue amplitude information into digital form and therafter determining the relative signal phase derived from the amplitude information to provide accurate timing information.

20. A method as claimed in claim 19, wherein the determining step initially determining the elapsed time between transmission and reception of the marker to allow this information to be used in combination with the phase information to more accurately determine this elapsed period.

21. A method as claimed in claim 19, including providing a switching step to allow the first and second transducers to be used for both transmission and reception and said determining step being provided to use timing information from both signal travel directions to determine the speed or flow rate of the fluid.

22. A method as claimed in claim 21, wherein a matching step is provided which is shared for both transmission and reception for each of the transducers to ensure the transducer characteristics are substantially constant for both modes of operation.

23. A fluid speed measurement device comprising: first and second spaced transducer means; transmitter and receiving means for transmitting and receiving signals in both direction between said transducer means; switching means for allowing each transducer means to be periodically used for either transmission or reception; and matching means commonly used for both transmission and reception to ensure that transducer characteristics are substantially constant for both transmitting and receiving modes of operation.

24. A device as claimed in claim 23, wherein the matching means includes a substantially constant low impedance path for each transducer both during transmission and reception.

25. A device as claimed in claim 24, wherein the low impedance path includes a network having a transformer with one winding for receiving an induced transmission signal for driving the transducer, said transformer winding also forming a series connection to the reception circuit when connected thereto.

26. A fluid speed measurement device comprising:

first and second spaced transducer means;

transmitter and receiving means for transmitting and receiving signals in both directions between said transducer means;

switching means for allowing each transducer means to be periodically used for either transmission or reception; and matching means for transmission and reception to ensure that transducer characteristics are substantially constant for both transmitting and receiving modes of operation;

wherein the matching means includes a substantially constant low impedance path for each transducer both during transmission and reception;

wherein the low impedance path includes a network having a transformer with one winding for receiving an induced transmission signal for driving the transducer, said transformer winding also forming a series connection to the reception circuit when connected thereto; and wherein the network includes a matching resistor in series with the transformer winding and a capacitor connected across the transducer to optimize phase coherance.

27. A device as claimed in claim 25 or 26, including a transducer driving circuit for providing the induced transformer signal and wherein a constant current regulator is provided for the driving circuit to reduce impedance variation in the matching network during transmission.

28. A device as claimed in any one of claims 23 to 26, wherein the transmitter means is arranged to generate a signal comprising a series of cycles or pulses with a phase change thereon acting as a timing marker and the receiver means being arranged to detect a phase change indicative of the marker.

29. A device as claimed in claim 28, wherein retaining means are provided for retaining amplitude information on the received signal to assist in measuring fluid speed.

30. A device as claimed in claim 29, wherein the retaining means include a plurality of sampling capacitors.

31. A device as claimed in any one of claims 23 to 26, wherein computation means are provided to determine fluid speed from timing information derived from the returning signal.

* * * * *